(12) United States Patent
Garrison et al.

(10) Patent No.: US 8,968,360 B2
(45) Date of Patent: Mar. 3, 2015

(54) SURGICAL INSTRUMENT WITH RESILIENT DRIVING MEMBER AND RELATED METHODS OF USE

(75) Inventors: David M. Garrison, Longmont, CO (US); James D. Allen, IV, Broomfield, CO (US); Jeffrey R. Unger, Longmont, CO (US); Duane E. Kerr, Loveland, CO (US); Sean T. O'Neill, Campbell, CA (US); Peter M. Mueller, Frederick, CO (US); Kim V. Brandt, Loveland, CO (US); James S. Cunningham, Boulder, CO (US); Keir Hart, Lafayette, CO (US); Daniel A. Joseph, Golden, CO (US); Jason T. Sanders, Johnstown, CO (US); Robert M. Sharp, Boulder, CO (US)

(73) Assignee: Covidien LP, Mansfield, MA (US)

(*) Notice: Subject to any disclaimer, the term of this patent is extended or adjusted under 35 U.S.C. 154(b) by 510 days.

(21) Appl. No.: 13/357,979

(22) Filed: Jan. 25, 2012

(65) Prior Publication Data

US 2013/0190753 A1    Jul. 25, 2013

(51) Int. Cl.
*A61B 18/14* (2006.01)
(52) U.S. Cl.
USPC ............................................. 606/208
(58) Field of Classification Search
USPC .................... 606/205–209, 32–52
See application file for complete search history.

(56) References Cited

U.S. PATENT DOCUMENTS

| D249,549 S | 9/1978 | Pike |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,269,780 A | 12/1993 | Roos |
| D343,453 S | 1/1994 | Noda |
| D348,930 S | 7/1994 | Olson |
| 5,330,471 A | 7/1994 | Eggers |
| D349,341 S | 8/1994 | Lichtman et al. |
| D354,564 S | 1/1995 | Medema |
| 5,391,166 A | 2/1995 | Eggers |
| 5,403,312 A | 4/1995 | Yates et al. |
| D358,887 S | 5/1995 | Feinberg |
| 5,496,347 A | 3/1996 | Hashiguchi et al. |

(Continued)

FOREIGN PATENT DOCUMENTS

| CN | 201299462 | 9/2009 |
|---|---|---|
| DE | 2415263 | 10/1975 |

(Continued)

OTHER PUBLICATIONS

Partial European Search Report 13152672.5 dated Jun. 11, 2013.

(Continued)

*Primary Examiner* — Scott Getzow

(57) ABSTRACT

A forceps is provided and includes a housing having a shaft. An end effector assembly operatively connects to a distal end of the shaft and includes a pair of first and second jaw members. One or both of the first and second jaw members is movable relative to the other jaw member from a clamping position to an open position. A resilient member operably couples to at least one of the first and second jaw members. The resilient member is configured to bias the first and second jaw members in the clamping position and provide a closure force on tissue disposed therebetween.

19 Claims, 12 Drawing Sheets

(56) References Cited

U.S. PATENT DOCUMENTS

| | | |
|---|---|---|
| 5,507,297 A | 4/1996 | Slater |
| 5,575,799 A | 11/1996 | Bolanos et al. |
| 5,599,350 A | 2/1997 | Schulze et al. |
| 5,618,307 A | 4/1997 | Donlon et al. |
| 5,624,452 A | 4/1997 | Yates |
| 5,626,607 A | 5/1997 | Malecki et al. |
| D384,413 S | 9/1997 | Zlock et al. |
| 5,688,270 A | 11/1997 | Yates et al. |
| 5,690,652 A | 11/1997 | Wurster et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,766,170 A | 6/1998 | Eggers |
| 5,769,849 A | 6/1998 | Eggers |
| H1745 H | 8/1998 | Paraschac |
| 5,797,941 A | 8/1998 | Schulze et al. |
| 5,807,393 A | 9/1998 | Williamson, IV et al. |
| 5,810,811 A | 9/1998 | Yates et al. |
| 5,833,690 A | 11/1998 | Yates et al. |
| D402,028 S | 12/1998 | Grimm et al. |
| 5,876,401 A | 3/1999 | Schulze et al. |
| D408,018 S | 4/1999 | McNaughton |
| D416,089 S | 11/1999 | Barton et al. |
| 6,024,741 A | 2/2000 | Williamson, IV et al. |
| D424,694 S | 5/2000 | Tetzlaff et al. |
| D425,201 S | 5/2000 | Tetzlaff et al. |
| 6,083,223 A | 7/2000 | Baker |
| H1904 H | 10/2000 | Yates et al. |
| 6,139,563 A | 10/2000 | Cosgrove, III et al. |
| 6,273,887 B1 | 8/2001 | Yamauchi |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,419,675 B1 | 7/2002 | Gallo, Sr. |
| 6,458,130 B1 | 10/2002 | Frazier et al. |
| D465,281 S | 11/2002 | Lang |
| D466,209 S | 11/2002 | Bon |
| 6,482,205 B1 | 11/2002 | Bonnet |
| 6,511,480 B1 | 1/2003 | Tetzlaff et al. |
| 6,585,735 B1 | 7/2003 | Frazier et al. |
| 6,676,660 B2 | 1/2004 | Wampler et al. |
| 6,682,528 B2 | 1/2004 | Frazier et al. |
| D493,888 S | 8/2004 | Reschke |
| D496,997 S | 10/2004 | Dycus et al. |
| D499,181 S | 11/2004 | Dycus et al. |
| 6,821,285 B2 | 11/2004 | Laufer et al. |
| D502,994 S | 3/2005 | Blake, III |
| D509,297 S | 9/2005 | Wells |
| 6,981,628 B2 | 1/2006 | Wales |
| D525,361 S | 7/2006 | Hushka |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| D531,311 S | 10/2006 | Guerra et al. |
| 7,118,570 B2 | 10/2006 | Tetzlaff et al. |
| 7,118,587 B2 | 10/2006 | Dycus et al. |
| 7,131,970 B2 | 11/2006 | Moses et al. |
| 7,131,971 B2 | 11/2006 | Dycus et al. |
| D533,274 S | 12/2006 | Visconti et al. |
| D533,942 S | 12/2006 | Kerr et al. |
| D535,027 S | 1/2007 | James et al. |
| 7,160,299 B2 | 1/2007 | Baily |
| D538,932 S | 3/2007 | Malik |
| 7,195,631 B2 | 3/2007 | Dumbauld |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| 7,232,440 B2 | 6/2007 | Dumbauld et al. |
| D547,154 S | 7/2007 | Lee |
| 7,255,697 B2 | 8/2007 | Dycus et al. |
| D564,662 S | 3/2008 | Moses et al. |
| D567,943 S | 4/2008 | Moses et al. |
| 7,367,976 B2 | 5/2008 | Lawes et al. |
| 7,384,420 B2 | 6/2008 | Dycus et al. |
| 7,384,421 B2 | 6/2008 | Hushka |
| D575,395 S | 8/2008 | Hushka |
| D575,401 S | 8/2008 | Hixson et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,473,253 B2 | 1/2009 | Dycus et al. |
| 7,481,810 B2 | 1/2009 | Dumbauld et al. |
| 7,500,975 B2 | 3/2009 | Cunningham et al. |
| 7,628,792 B2 | 12/2009 | Guerra |
| 7,655,007 B2 | 2/2010 | Baily |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| 7,789,878 B2 | 9/2010 | Dumbauld et al. |
| D627,462 S | 11/2010 | Kingsley |
| D628,289 S | 11/2010 | Romero |
| D628,290 S | 11/2010 | Romero |
| 7,846,161 B2 | 12/2010 | Dumbauld et al. |
| D630,324 S | 1/2011 | Reschke |
| 7,879,035 B2 | 2/2011 | Garrison et al. |
| 7,905,881 B2 | 3/2011 | Masuda et al. |
| 7,922,718 B2 | 4/2011 | Moses et al. |
| 7,935,052 B2 | 5/2011 | Dumbauld |
| D649,249 S | 11/2011 | Guerra |
| D649,643 S | 11/2011 | Allen, IV et al. |
| 2002/0080793 A1 | 6/2002 | Kim |
| 2002/0080795 A1 | 6/2002 | Van Wageningen et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0018331 A1 | 1/2003 | Dycus et al. |
| 2003/0109875 A1 | 6/2003 | Tetzlaff et al. |
| 2003/0139742 A1 | 7/2003 | Wampler et al. |
| 2003/0181910 A1 | 9/2003 | Dycus et al. |
| 2003/0229344 A1 | 12/2003 | Dycus et al. |
| 2004/0082952 A1 | 4/2004 | Dycus et al. |
| 2004/0087943 A1 | 5/2004 | Dycus et al. |
| 2004/0116924 A1 | 6/2004 | Dycus et al. |
| 2004/0243125 A1 | 12/2004 | Dycus et al. |
| 2005/0004569 A1 | 1/2005 | Witt et al. |
| 2006/0074417 A1 | 4/2006 | Cunningham et al. |
| 2006/0079890 A1 | 4/2006 | Guerra |
| 2006/0079933 A1 | 4/2006 | Hushka et al. |
| 2006/0084973 A1 | 4/2006 | Hushka |
| 2006/0189981 A1 | 8/2006 | Dycus et al. |
| 2006/0190035 A1 | 8/2006 | Hushka et al. |
| 2006/0259036 A1 | 11/2006 | Tetzlaff et al. |
| 2007/0062017 A1 | 3/2007 | Dycus et al. |
| 2007/0078458 A1 | 4/2007 | Dumbauld et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0142834 A1 | 6/2007 | Dumbauld |
| 2007/0156140 A1 | 7/2007 | Baily |
| 2007/0260242 A1 | 11/2007 | Dycus et al. |
| 2008/0033428 A1 | 2/2008 | Artale et al. |
| 2008/0319442 A1 | 12/2008 | Unger et al. |
| 2009/0012520 A1 | 1/2009 | Hixson et al. |
| 2009/0043304 A1 | 2/2009 | Tetzlaff et al. |
| 2009/0112206 A1 | 4/2009 | Dumbauld et al. |
| 2009/0149854 A1 | 6/2009 | Cunningham et al. |
| 2009/0171350 A1 | 7/2009 | Dycus et al. |
| 2009/0182327 A1 | 7/2009 | Unger |
| 2010/0094286 A1 | 4/2010 | Chojin |
| 2010/0100122 A1 | 4/2010 | Hinton |
| 2010/0130971 A1 | 5/2010 | Baily |
| 2010/0179545 A1 | 7/2010 | Twomey et al. |

(56) References Cited

U.S. PATENT DOCUMENTS

| | | | |
|---|---|---|---|
| 2010/0204697 A1 | 8/2010 | Dumbauld et al. | |
| 2010/0228249 A1 | 9/2010 | Mohr et al. | |
| 2010/0280515 A1 | 11/2010 | Hixson et al. | |
| 2011/0004209 A1 | 1/2011 | Lawes et al. | |
| 2011/0071522 A1 | 3/2011 | Dumbauld et al. | |
| 2011/0071525 A1 | 3/2011 | Dumbauld et al. | |
| 2011/0106079 A1 | 5/2011 | Garrison et al. | |
| 2011/0301604 A1* | 12/2011 | Horner et al. | 606/52 |
| 2011/0301637 A1 | 12/2011 | Kerr | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 02617 | 12/2005 |
| DE | 20 2007 00916 | 10/2007 |
| DE | 20 2007 00931 | 10/2007 |
| DE | 20 2007 01623 | 3/2008 |
| DE | 19738457 | 1/2009 |
| DE | 10 2008 01840 | 7/2009 |
| EP | 0 518 230 | 5/1996 |
| EP | 0 878 169 | 11/1998 |
| EP | 1159926 | 12/2001 |
| EP | 1 532 932 | 5/2005 |
| EP | 1 301 135 | 9/2005 |
| EP | 0 875 209 | 5/2006 |
| EP | 1 330 991 | 9/2007 |
| EP | 1 929 970 | 6/2008 |
| EP | 1 530 952 | 1/2010 |
| EP | 1 535 581 | 7/2010 |
| EP | 1 649 821 | 12/2011 |
| EP | 2 392 282 | 12/2011 |
| EP | 1 769 765 | 3/2012 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 94/08524 | 4/1994 |
| WO | WO 00/24330 | 5/2000 |
| WO | WO 00/36986 | 6/2000 |
| WO | WO 00/59392 | 10/2000 |
| WO | WO 01/15614 | 3/2001 |
| WO | WO 01/17448 | 3/2001 |
| WO | WO 01/54604 | 8/2001 |
| WO | WO 02/04331 | 1/2002 |
| WO | WO 02/07627 | 1/2002 |
| WO | WO 02/058544 | 8/2002 |
| WO | WO 02/080783 | 10/2002 |
| WO | WO 02/080794 | 10/2002 |
| WO | WO 02/080796 | 10/2002 |
| WO | WO 02/080799 | 10/2002 |
| WO | WO 2004/073490 | 9/2004 |
| WO | WO 2005/110264 | 11/2005 |
| WO | WO 2008/045348 | 4/2008 |
| WO | WO 2008/045350 | 4/2008 |
| WO | WO2009/039179 | 3/2009 |
| WO | WO 2010/104753 | 9/2010 |
| WO | WO2011/018154 | 2/2011 |

OTHER PUBLICATIONS

Extended European Search Report 13152672.5 dated Aug. 29, 2013.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.

(56) References Cited

OTHER PUBLICATIONS

U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.

(56) References Cited

OTHER PUBLICATIONS

Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

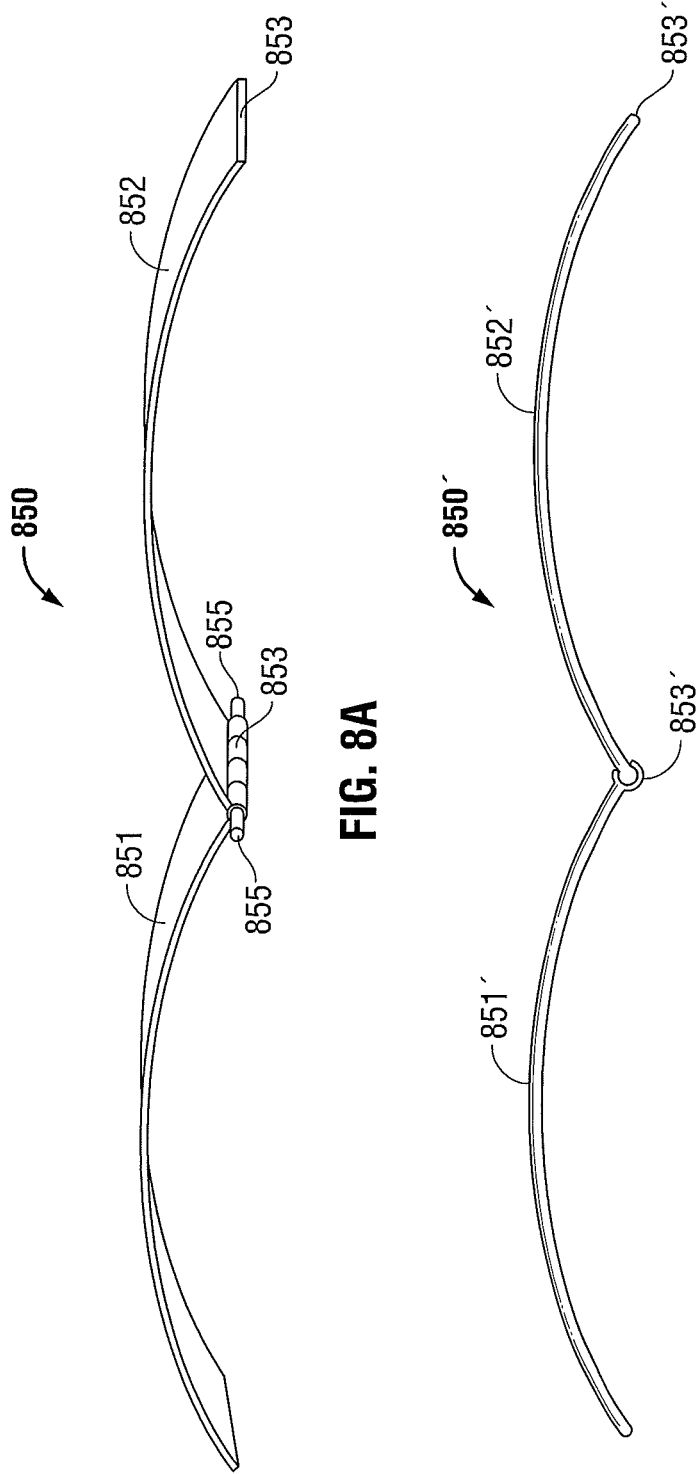

SURGICAL INSTRUMENT WITH RESILIENT DRIVING MEMBER AND RELATED METHODS OF USE

BACKGROUND

1. Technical Field

The present disclosure relates to an apparatus for performing an electrosurgical procedure. More particularly, the present disclosure relates to an electrosurgical apparatus including an end effector drive assembly that includes a resilient coupling member configured to modulate a clamping force of the end effector.

2. Description of Related Art

Electrosurgical instruments, e.g., electrosurgical forceps (open or closed type), are well known in the medical arts and typically include a housing, a handle assembly, a shaft and an end effector assembly attached to a distal end of the shaft. The end effector includes jaw members configured to manipulate tissue (e.g., grasp and seal tissue). Typically, the electrosurgical forceps utilizes both mechanical clamping action and electrical energy to effect hemostasis by heating the tissue and blood vessels to coagulate, cauterize, seal, cut, desiccate, and/or fulgurate tissue. One or more driving mechanisms, e.g., a drive assembly including a drive rod, is utilized to cooperate with one or more components operatively associated with the end effector to impart movement to one or both of the jaw members.

In certain instances, to facilitate moving the jaw members from an open position for grasping tissue to a closed position for clamping tissue (or vice versa) such that a consistent, uniform tissue effect (e.g., tissue seal) is achieved, one or more types of suitable devices may be operably associated with the electrosurgical forceps. For example, in some instances, one or more types of springs, e.g., a compression spring, may operably couple to the handle assembly associated with the electrosurgical forceps. In this instance, the spring is typically operatively associated with the drive assembly to facilitate actuation of a movable handle associated with the handle assembly to ensure that a specific closure force between the jaw members is maintained within one or more suitable working ranges.

In certain instances, the shaft may bend or deform during the course of an electrosurgical procedure. For example, under certain circumstances, a clinician may intentionally bend or articulate the shaft to gain desired mechanical advantage at the surgical site. Or, under certain circumstances, the surgical environment may cause unintentional or unwanted bending or flexing of the shaft, such as, for example, in the instance where the shaft is a component of a catheter-based electrosurgical forceps. More particularly, shafts associated with catheter-based electrosurgical forceps are typically designed to function with relatively small jaw members, e.g., jaw members that are configured to pass through openings that are 3 mm or less in diameter. Accordingly, the shaft and operative components associated therewith, e.g., a drive rod, are proportioned appropriately. That is, the shaft and drive rod are relatively small.

As can be appreciated, when the shaft is bent or deformed (either intentionally or unintentionally) the frictional losses associated with drive rod translating through the shaft are transferred to the spring in the housing, which, in turn, may diminish, impede and/or prevent effective transfer of the desired closure force that is needed at the jaw members. Moreover, the frictional losses may also lessen the operative life of the spring, which, in turn, ultimately lessens the operative life of the electrosurgical instrument

SUMMARY

The present disclosure provides an endoscopic forceps. In some aspects, the disclosed forceps include an elongate shaft having a proximal end and a distal end. The disclosed forceps include an end effector assembly disposed at a distal end of the shaft. The end effector assembly includes a pair of first and second jaw members, wherein at least one of the first and second jaw members are movable relative to the other from a clamping position, wherein the first and second jaw members cooperate to grasp tissue therebetween, to an open position wherein the first and second jaw members are disposed in spaced relation relative to one another. The disclosed forceps includes a cam member configured to translate along a longitudinal axis of the shaft and a drive rod configured to translate along a longitudinal axis of the shaft. A resilient member couples a distal end of the of the drive rod to a proximal end of the cam member. At least one of the first and second jaw members includes at least one cam slot defined therein that is configured to receive the cam member, that, upon movement thereof, rotates the first and second jaw members from the clamping position to the open position.

In some aspects, the disclosed forceps includes a housing having a shaft that extends therefrom defining a longitudinal axis therethrough. The disclosed forceps include an end effector assembly operatively connected to a distal end of the shaft, and includes a first jaw member and a second jaw member. The first jaw member is movable relative to the second jaw member from an open position wherein the first and second jaw members are disposed in spaced relation relative to one another to a closed or clamping position wherein the first and second jaw members cooperate to grasp tissue therebetween. A resilient member is operably coupled to the first jaw member and is configured to bias the first jaw member toward the open position. A hinged spring is operably coupled at a distal end thereof to the first jaw member. A handle extending from the housing is operably coupled to a proximal end of the hinged spring and configured to translate a proximal end of the hinged string along the longitudinal axis of the housing. The hinged spring may include at least a proximal portion and a distal portion operably coupled by a hinge.

The disclosed structures, arrangements, and methods may be advantageously employed in any suitable instrument now or the future known, including without limitation, a laparoscopic forceps, an open forceps, vessel sealing instruments, vessel harvesting instruments, and so forth.

Also disclosed is a method for performing a surgical procedure. The method includes providing an endoscopic instrument as disclosed hereinabove, moving one or more jaw members to the open position; positioning tissue between the first and second jaw members; and moving the jaw members to the clamping position. Additionally the method may include sealing tissue when the jaw members are moved to, or in, the clamping position, and, additionally or alternatively, delivering electrosurgical energy to tissue.

BRIEF DESCRIPTION OF THE DRAWINGS

Various embodiments of the present disclosure are described hereinbelow with references to the drawings, wherein:

FIG. 8A is a side, oblique view of a spring in accordance with the present disclosure having a piano hinge and a generally rectangular cross-section;

FIG. 8B is a side, oblique view of a hinged spring in accordance with the present disclosure having a ball and socket hinge and a generally circular cross-section.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
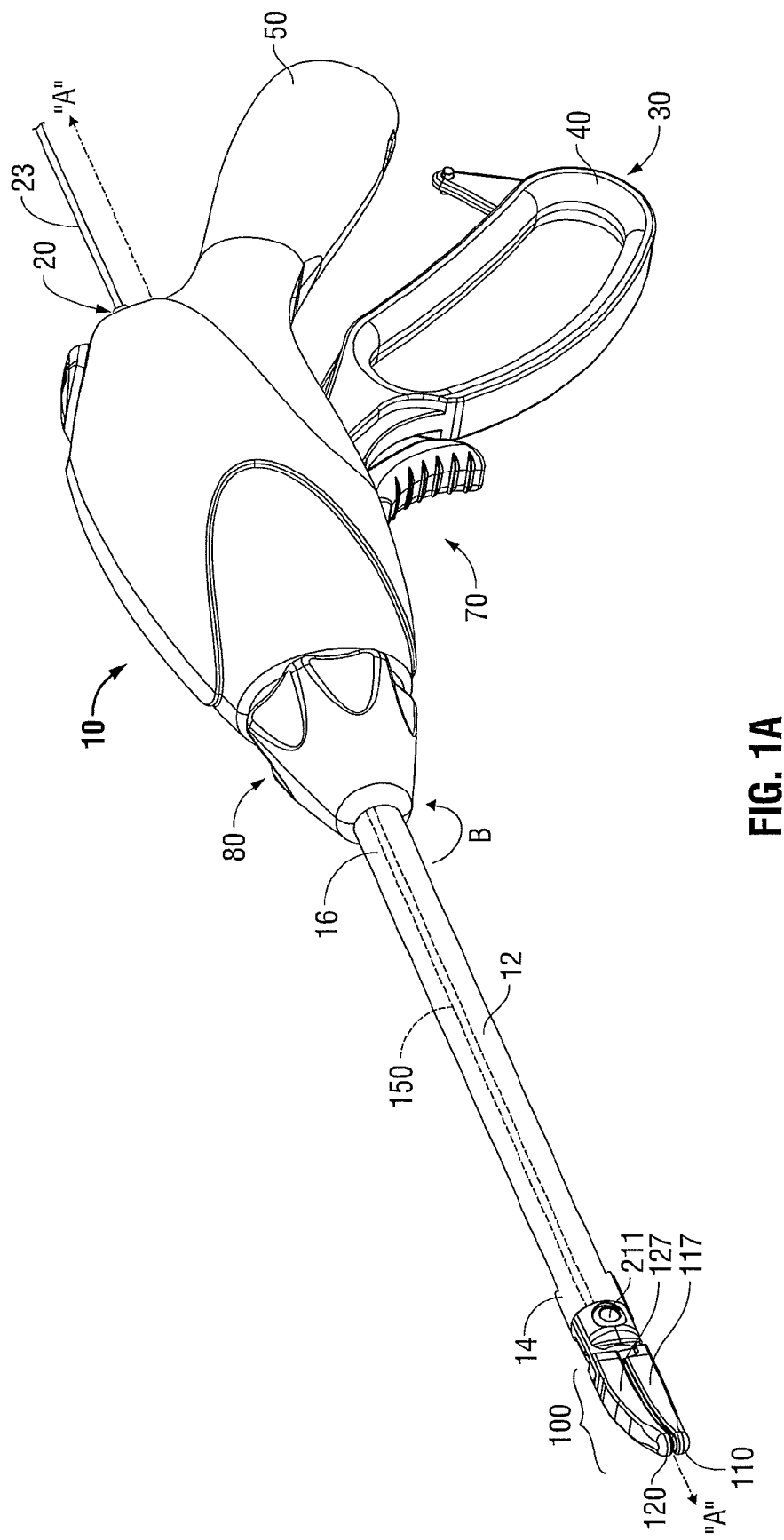
FIG. 1A is a side, perspective view of an endoscopic bipolar forceps showing an end effector assembly including jaw members in a closed configuration according to an embodiment of the present disclosure.
Figure 1B:
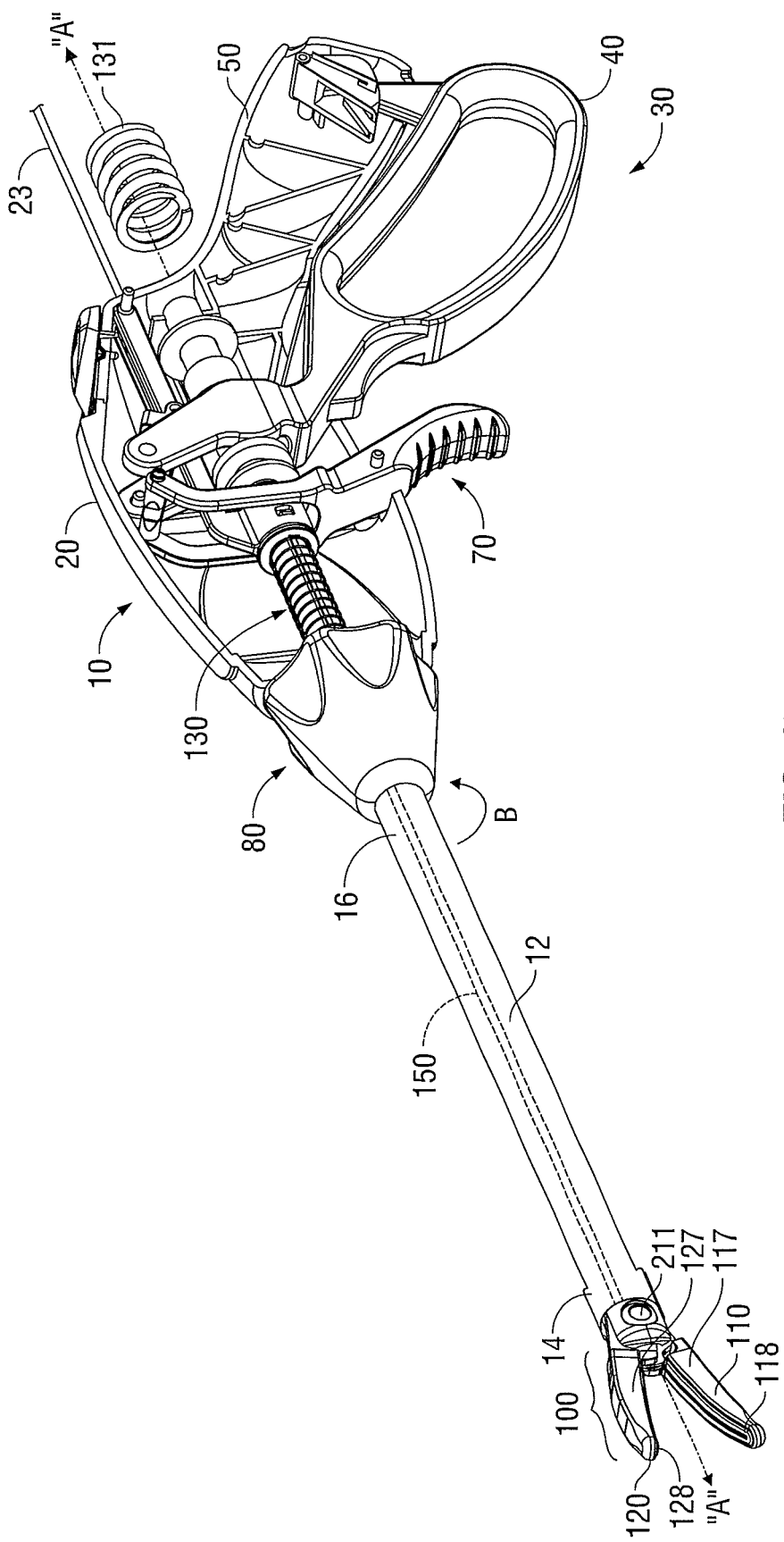
FIG. 1B is a side, perspective view of the endoscopic bipolar forceps depicted in FIG. 1A illustrating internal components of a handle assembly associated with the endoscopic bipolar forceps.

With reference to FIGS. 1A and 1B, an illustrative embodiment of an electrosurgical apparatus, e.g., a bipolar forceps 10 is shown. Forceps 10 is operatively and selectively coupled to a suitable power source, such as, for example, an electrosurgical generator (not shown) for performing an electrosurgical procedure. As noted above, an electrosurgical procedure may include sealing, cutting, cauterizing coagulating, desiccating, and fulgurating tissue all of which may employ RF energy. The generator may be configured for monopolar and/or bipolar modes of operation. The generator may include or is in operative communication with a system 1 (FIG. 9) that may include one or more processors in operative communication with one or more control modules that are executable on the processor. The control module (not explicitly shown) may be configured to instruct one or more modules to transmit electrosurgical energy, which may be in the form of a wave or signal/pulse, via one or more cables (e.g., cable 23) to the forceps 10.

Forceps 10 is shown configured for use with various electrosurgical procedures and generally includes a housing 20, electrosurgical cable 23 that connects the forceps 10 to a source of electrosurgical energy, e.g., electrosurgical generator 2, a handle assembly 30, a rotating assembly 80, a trigger assembly 70, a drive assembly 130, and an end effector assembly 100 that operatively connects to a drive element 150 of the drive assembly 130 (see FIG. 1B). End effector assembly 100 includes opposing jaw members 110 and 120 (FIGS. 1A and 1B) that mutually cooperate to grasp, seal, and in some cases, divide large tubular vessels and large vascular tissues. One or both electrically conductive seal plates 118 and 128 are electrically coupled to a conductor of electrosurgical cable 23 by one or more lead wires (not explicitly shown) to facilitate delivery of electrosurgical energy from generator 2 to targeted tissue. The drive assembly 130 is in operative communication with handle assembly 30 for imparting movement of one or both of a pair of jaw members 110, 120 of end effector assembly 100. Conventional drive assemblies typically utilize one or more types of springs, e.g., a compression spring 131, to facilitate closing the jaw members 110 and 120. For illustrative purposes, compression spring 131 (see FIG. 1B) is shown separated from the housing 20.

With continued reference to FIGS. 1A and 1B, forceps 10 includes a shaft 12 that has a distal end 14 configured to mechanically engage the end effector assembly 100 and a proximal end 16 that mechanically engages the housing 20. In the drawings and in the descriptions that follow, the term "proximal," as is traditional, will refer to the end of the forceps 10 which is closer to the user, while the term "distal" will refer to the end that is farther from the user.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is ultimately connected to the drive assembly 130, which together mechanically cooperate to impart movement of one or both of the jaw members 110 and 120 to move from a clamping or closed position (FIG. 1A), wherein the jaw members 110 and 120 cooperate to grasp tissue therebetween, to an open position (FIG. 1B), wherein the jaw members 110 and 120 are disposed in spaced relation relative to one another.

Jaw members 110, 120 are operatively and pivotably coupled to each other and located adjacent the distal end 14 of shaft 12. Respective electrically conductive seal plates 118 and 128 are operably supported on and secured to respective jaw housings 117 and 127 of respective the jaw members 110 and 120, described in greater detail below. For the purposes herein, jaw members 110 and 120 include jaw housings 117 and 127 that are configured to support sealing plates 118 and 128, respectively.

For a more detailed description of the forceps 10 including handle assembly 30 including movable handle 40, rotating assembly 80, trigger assembly 70, drive assembly 130, jaw members 110 and 120 (including coupling methods utilized to pivotably couple the jaw members 110 and 120 to each other) and electrosurgical cable 23 (including line-feed configurations and/or connections), reference is made to commonly-owned U.S. Pat. No. 7,766,910 issued on Aug. 3, 2010.

Figure 2:
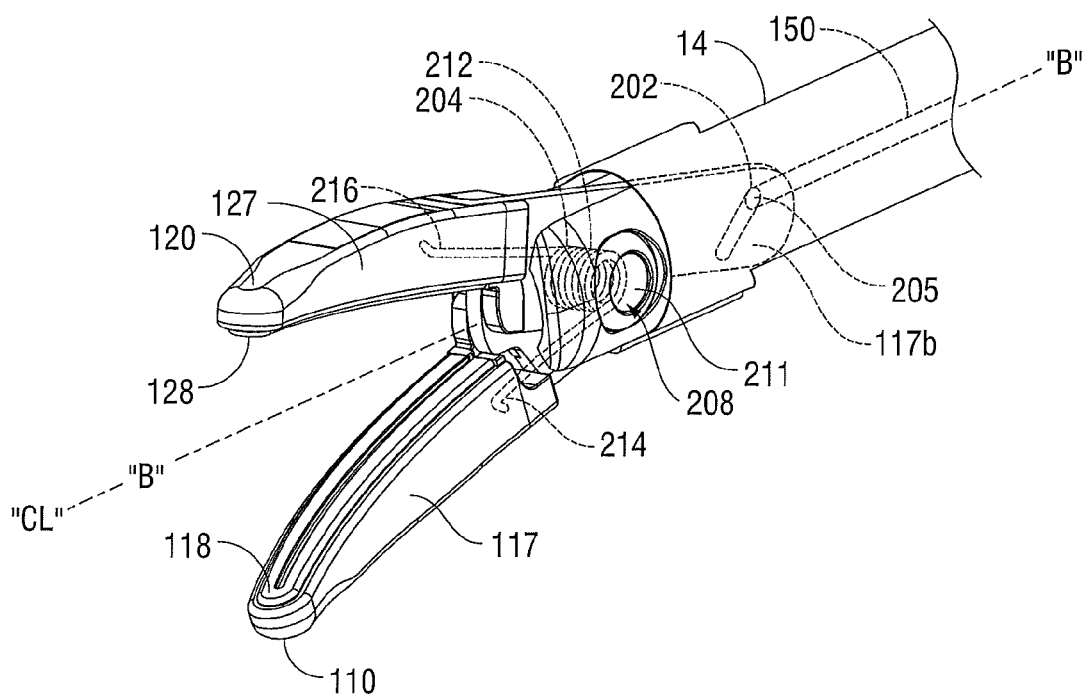
FIG. 2 is an enlarged, schematic view of the jaw members depicted in FIGS. 1A and 1B.

Turning now to FIG. 2, one embodiment of jaw housings 117 and 127 is shown. It should be noted that in accordance with the present disclosure one or both of the jaw housings 117 and 127 may include a proximal end that is configured to support one or more cam slots 202 and resilient members 204 to facilitate closing in of the jaw members 110 and 120. Jaw members 110 and 120 are substantially identical to each other, and, in view thereof, and so as not to obscure the present disclosure with redundant information, the operative components associated with the jaw housing 117 are described in further detail with respect to jaw member 110, and only those features distinct to jaw member 120 and jaw housing 127 will be described hereinafter.

With continued reference to FIG. 2, jaw member 110, jaw housing 117, and operative components associated therewith may be formed from any suitable material, including but not limited to metal, metal alloys, plastic, plastic composites, etc. In the embodiment illustrated in FIG. 2, jaw member 110 is formed from metal.

Jaw housing 117 of jaw member 110 is configured to securely engage the electrically conductive seal plate 118. A portion of a proximal flange 117b of the jaw member 110 is operably secured to the distal end 14 of the shaft 12. More particularly, a portion of proximal flange 117b operably couples to the distal end 14 and is in operative communication with the drive element 150 of the drive assembly 130 such that movement of the drive element 150 causes one or both of the jaw members 110 and 120 to move from the closed or clamping position to the open position and vice versa. For example, in one particular embodiment, when the drive element 150 is "pulled," i.e., moved or translated proximally, one or both of the jaw members 110 and 120 is/are caused to move away from the other. Alternatively, and if desired, the drive assembly 130 including the drive element 150 may be configured such that when the drive element 150 is "pushed," i.e., moved or translated distally, one or both of the jaw members 110 and 120 are caused to move away from each other. In certain instances, it may prove useful to have a drive element 150 that is flexible. More particularly, where the drive element 150 is operatively associated with an endoluminal instrument, the drive element 150 may be substantially flexible to accommodate bends typically associated with that type of instrument when the bipolar forceps 10 is remotely actuatable relative to the patient.

In the illustrated embodiment, proximal flange 117b of the jaw housing 110 includes a generally elongated configuration that may be rectangular, circumferential or a combination thereof in shape.

Proximal end 117b of the jaw member 110 includes one or more cam slots 202 defined therein that support one or more cam members 205 (see FIG. 2). More particularly, cam slot 202 is of suitable proportion and configured to receive cam member 205 and is operably formed and/or positioned near the proximal flange 117b of the jaw housing 117. Cam slot 202 includes a generally oblique configuration with respect to a longitudinal axis "B-B" that is parallel to a longitudinal axis "A-A" defined through the shaft 12, see FIGS. 1A and 2. Cam slot 202 may extend at an angle that ranges from about 5° to about 60° with respect to the longitudinal axis "B-B." In the embodiment illustrated FIG. 2, cam slot 202 extends at an angle that is approximately equal to 45° with respect to the longitudinal axis "B-B." The angle of the cam slot 202 may be selectively varied depending upon a particular instrument, use or manufacturing preference.

An opening 208 is defined in and extends through the proximal flange 117b of jaw housing 117 and is configured to receive a spring pin 211. Opening 208 is shown engaged with spring pin 211 and as such is not explicitly visible. In the embodiment illustrated in FIG. 2, a portion of the spring pin 211 is dimensioned to securely engage the resilient member 204 (shown in phantom).

One or more types of resilient members 204 may be operably associated with the housing 117 and include, for example, a torsion spring that is utilized to generate a closure force on the jaw members 110 and 120 when the jaw members 110 and 120 are in a closed or clamped position. The resilient member 204 cooperates with the drive assembly 130 to provide the necessary closure force on the jaw members 110 and 120 for sealing tissue, e.g., in the range of about 3 kg/cm$^2$ to about 16 kg/cm$^2$.

Resilient member 204 operably engages jaw housings 117 and 127 and is biased in a closed orientation. More particularly, a proximal end 212 of suitable proportion and having a generally circumferential configuration is dimensioned to securely couple to the spring pin 211. Two generally elongated fingers 214 and 216 (shown in phantom) extend from proximal end 212 adjacent the proximal ends of the jaw members, e.g., proximal flange 117b of jaw member 110 and a proximal flange (not explicitly shown) of the jaw member 120, and fixedly couple to a respective jaw member, e.g., jaw member 117 and jaw member 120. In the embodiment illustrated in FIG. 2, the resilient member 204 biases the jaw members 110 and 120 toward each other to a closed position such that a consistent uniform seal pressure is generated to effectively seal tissue. More particularly, the configuration of the resilient member 204 is designed such that each the elongated fingers 214 and 216 are operably disposed adjacent a respective imaginary center-line "CL" that extends through each of the jaw members 110 and 120, see FIG. 2. In this instance, the force from each of the elongated fingers 214 and 216 is evenly distributed to and throughout each respective jaw member.

One or more types of lubricious materials (not shown), e.g., polytetrafluoroethylene (PTFE), may coat cam slot 202 or an inner peripheral surface thereof. Coating the cam slot 202 with the lubricious material facilitates movement of the cam member 205 within the cam slot 202 when the drive element 150 is translated proximally (or distally depending on a particular configuration).

In an assembled configuration each of the jaw members 110 and 120 is positioned in side-by-side relation. Cam member 205 is operably disposed within cam slot 202 associated with jaw member 110 and a corresponding cam slot (not explicitly shown) associated with jaw member 120. Spring pin 211 is positioned within the opening associated with jaw member 110 and a corresponding opening (not explicitly shown) associated with jaw member 120. As noted above, the spring pin 211 provides a pivot for each of the jaw members 110 and 120. Once assembled, the jaw members 110 and 120 may be pivotably supported at the distal end 14 of the shaft 12 by known methods, such as, for example, by the method described in commonly-owned U.S. Patent Publication No. 2007/0260242 filed on Jul. 11, 2007.

In use, initially jaw members 110 and 120 are biased in a closed position under the closure and/or sealing force provided by the resilient member 204. Proximal movement of movable handle 40 causes the drive element 150 to move proximally. Proximal movement of the drive element 150 causes cam member 205 positioned within the cam slot 202 to move proximally against the bias of the resilient member 204, which, in turn, causes both of the jaw members 110 and 120 to move relative to one another, such that tissue is positionable between the jaw members 110 and 120. Once tissue is positioned between the jaw members 110 and 120 the movable handle 40 is released, which, in turn, causes the jaw members 110 and 120 to move toward one another under the biasing force of the resilient member 204 which generates a sealing or closure force on the tissue disposed between the jaw members 110 and 120. The resilient member 204 provides an additional mechanical advantage at the jaw members 110 and 120 and reduces any frictional losses that are typically associated with conventional forceps when a drive rod is translated within a shaft to make the necessary closure force to seal tissue, e.g., the closure force is offloaded and/or diminished by the resilient member 204.

Figure 3A:
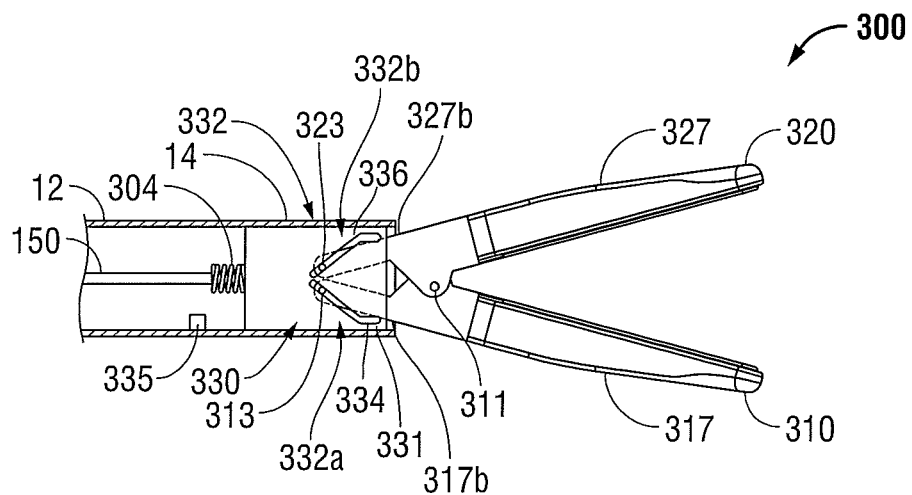
FIGS. 3A and 3B are schematic views of jaw members operably coupled to a distal end of the endoscopic forceps depicted in FIGS. 1A and 1B according to another embodiment of the present disclosure.
Figure 3B:
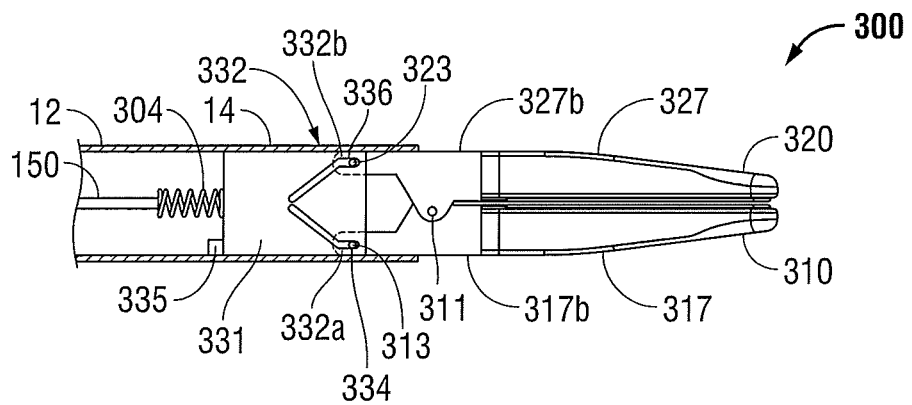

With reference to FIGS. 3A and 3B, another embodiment of an end effector 300 configured for use with the forceps 10 is illustrated. End effector 300 is substantially identical to end effector 100, and, in view thereof, and so as not to obscure the present disclosure with redundant information, only those features distinct to end effector 300 will be described hereinafter.

End effector 300 includes jaw members 310 and 320. As described above with respect to jaw members 110 and 120, jaw members 310 and 320 are pivotably coupled to each other via a spring pin or pivot pin 311. More particularly, pivot pin 311 operably couples the jaw members 310 and 320 about a medial portion of respective jaw housings 317 and 327 (FIG. 3A). Pivot pin 311 maintains the jaw members 310 and 320 in a substantially fixed position with respect to the longitudinal axis "A-A" when the jaw members 310 and 320 are pivoted or rotated about the pivot pin 311 (see FIGS. 1A and 1B). That is, the jaw members 310 and 320 do not translate along the longitudinal axis "A-A" when movable handle 40 is moved.

A respective cam follower 313 and 323 is operably disposed at a respective proximal end 317b and 327b of the jaw members 310 and 320, respectively. In the embodiment illustrated in FIGS. 3A and 3B, the cam followers 313 and 323 are configured to rotate the respective jaw members 310 and 320 from an open position (FIG. 3A) to a clamping position (FIG. 3B) when the movable handle 40 is moved proximally. Cam followers 313 and 323 are proportioned to movably couple to a cam assembly 330.

Cam assembly 330 translates or moves along the longitudinal axis "A-A" when the movable handle 40 is moved proximally and/or distally. To this end, cam assembly 330 is suitably shaped and proportioned to movably reside within the shaft 12 adjacent the distal end 14. For illustrative purposes, cam assembly 330 is shown elongated with a generally rectangular shape. One or more cam slots 332 are operably disposed on or defined in the cam assembly 330. In the embodiment illustrated in FIGS. 3A and 3B, two intersecting cam slots 332a and 332b are defined in the cam assembly 330. The cam slots 332a and 332b are proportioned to receive respective cam followers 313 and 323 such that cam followers 313 and 323 are movable along a length of the respective cam slots 332a and 332b.

Each of the cam slots 332a and 332b includes a respective distal end 334 and 336. The distal ends 334 and 336 are configured to function as latches. More particularly, the distal ends 334 and 336 maintain the respective cam followers 313 and 323 in a substantially fixed position after the movable handle 40 is moved a predetermined distance proximally and the jaw members 310 and 320 are in the clamping position.

For example, and in one particular embodiment, one or more stop members 335 may be operably disposed along an internal surface of the shaft 12. In this instance, stop member 335 may be configured to contact a portion, e.g., a bottom surface 331, of the cam assembly 330 when the movable handle 40 is moved through an "unlatching" stroke, see FIGS. 3A and 3B. Accordingly, when movable handle 40 is moved through the "unlatching" stroke, the stop member 335 contacts the bottom surface 331 of cam assembly 330, thereby defining the maximum proximal extent of the range of motion of cam assembly 330, which, in turn, defines the maximum opening dimension (e.g., maximum opening angle) of jaws 317, 327 (FIG. 3A). Other latching and unlatching devices and/or configurations may be utilized to latch and unlatch the cam followers 313 and 323 from the respective distal ends 334 and 336.

One or more types of resilient members 304 operably couple to the drive element 150 and to the cam assembly 330. Resilient member 304 may be any suitable resilient member, e.g., a compression spring. A distal end of the drive element 150 operably couples to a proximal end of the resilient member 304 and proximal end of the cam assembly 330 operably couples to a distal end of the resilient member 304. The resilient member 304 operably couples to the distal end of the drive element 150 and proximal end of the cam assembly 330 via any suitable coupling methods. As described above with resilient member 204, resilient member 304 cooperates with the drive assembly 130 to provide the necessary closure force on the jaw members 310 and 320 for sealing tissue, e.g., in the range of about 3 kg/cm$^2$ to about 16 kg/cm$^2$.

In use, initially jaw members 310 and 320 are biased in an open position (FIG. 3A). Tissue is positioned between the jaw members 310 and 320. Thereafter, the movable handle 40 is moved proximally causing the drive element 150 to move proximally. Proximal movement of the drive element 150 moves the resilient member 304 proximally, which, in turn, moves the cam assembly 330 proximally. Proximal movement of the cam assembly 330 causes the detents 313 and 323 to move within the respective cam slots 332a and 332b until the detents 313 and 323 are latched into a closed or clamping position (FIG. 3B). In the latched position, the requisite closure force is placed onto the tissue disposed between the jaw members 310 and 320. Thereafter, electrosurgical energy is transmitted to seal surfaces 318 and 328 operably associated with respective jaw members 310 and 320 such that a desired tissue effect, e.g., a tissue seal, may be achieved on the tissue disposed between the jaw members 310 and 320. To open the jaw members 310 and 320, the moveable handle 40 is moved through an "unlatching" stroke that retracts the cam followers 313 and 323 from the respective distal ends 334 and 336 such that the jaw members 310 and 320 return to the initial open position.

Figure 4A:
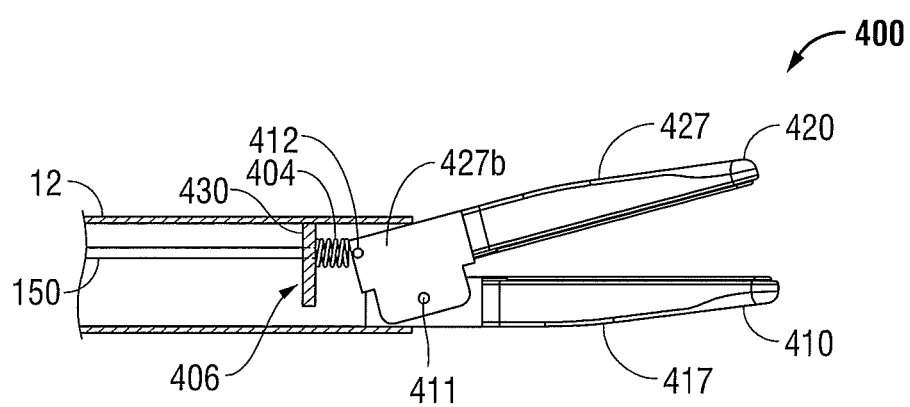
FIGS. 4A and 4B are schematic views of jaw members operably coupled to a distal end of the endoscopic forceps depicted in FIGS. 1A and 1B according to yet another embodiment of the present disclosure.
Figure 4B:
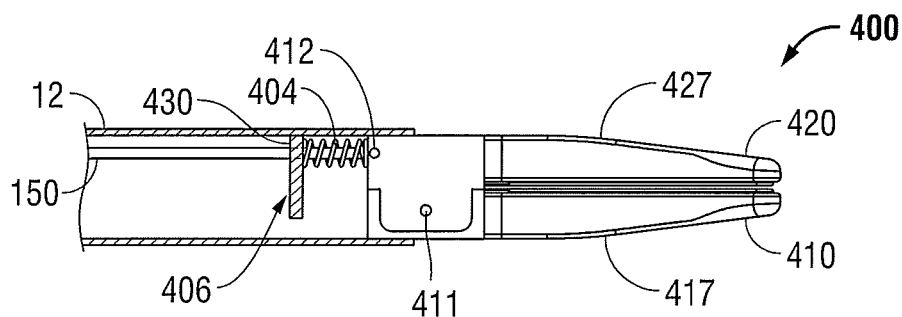

With reference to FIGS. 4A and 4B, another embodiment of an end effector 400 that is configured for use with the forceps 10 is illustrated. End effector 400 is substantially identical to end effectors 100 and 300, and, in view thereof, and so as not to obscure the present disclosure with redundant information, only those features distinct to end effector 400 will be described hereinafter.

End effector 400 includes jaw members 410 and 420. In the embodiment illustrated in FIGS. 4A and 4B, one of the jaw members, e.g., jaw members 420, is movable, and one of the jaw members, e.g., jaw member 410, is stationary. This configuration of jaw members 420 and 410 may be reversed to accommodate various surgical procedures. Jaw members 410 and 420 are pivotably coupled to one another via a pivot pin 411.

A support structure 430 is operably disposed along an internal frame of the shaft 12 adjacent the distal end 14. More particularly, the support structure 430 is operably coupled to a top portion of the internal frame of the shaft 12. Support structure 430 is configured to mechanically communicate with a resilient member 404. More particularly, the support structure 430 provides a substantially rigid surface that is configured to compress the resilient member 404 when the resilient member 404 is moved proximally and the movable jaw member 420 is moved to the open position. To this end, support structure 430 may have any suitable shape. In the embodiment illustrated in FIGS. 4A and 4B, support structure 430 includes a generally circumferential configuration having an aperture 406 of suitable proportion defined therethrough. Aperture 406 includes a diameter that is sized to receive the drive element 150 (or portion thereof) that includes a distal end that operably couples to a proximal end 427b of the movable jaw member 420. More particularly, the diameter of the aperture 406 is such that the drive element 150 is movable through the aperture 406 when the movable handle 40 is moved proximally and/or distally. Additionally, the aperture 406 is proportioned such that the resilient member 404 is prevented from translating therethrough when the movable handle 40 is moved proximally and/or distally.

In the embodiment illustrated in FIGS. 4A and 4B, the support structure 430 is configured to maintain the drive element 150 in a substantially fixed off-set orientation above the pivot pin 411, see FIG. 4A, for example. Having the support structure 430 configured in such a manner facilitates moving the jaw member 420 about the pivot pin 411.

Resilient member 404 is operably disposed between the support structure 430 and the proximal end 427b of the jaw housing 427. In an uncompressed state, resilient member 404 cooperates with the support structure 430 to provide the necessary closure force on the jaw members 410 and 420 for sealing tissue, e.g., in the range of about 3 kg/cm$^2$ to about 16 kg/cm$^2$. To this end, the resilient member 404 may be any suitable resilient spring, e.g., a compression spring 404, including, but not limited to those previously described herein. The compression spring 404 is proportioned such that the drive element 150 is positionable therethrough, FIG. 4A.

In use, initially jaw members 410 and 420 are biased in a closed position under the closure and/or sealing force provided by the compression spring 404 (FIG. 4B). Proximal movement of movable handle 40 causes the drive element 150 to move proximally. Proximal movement of the drive element 150 causes the moveable jaw member, e.g., jaw member 420, to move relative to the stationary jaw member, e.g., jaw member 410, such that tissue may be positioned between the jaw members 410 and 420. Once tissue is positioned between the jaw members 410 and 420 the movable handle 40 is released, which, in turn, causes the jaw member 420 to move toward jaw member 410 under the biasing force of the compression spring 404 which generates a closure force on the tissue disposed between the jaw members 410 and 420. The compression spring 404 provides an additional mechanical advantage at the jaw members 410 and 420 and reduces the frictional losses that are typically associated with conventional forceps when a drive rod is translated within a shaft to make the necessary closure force to seal tissue, e.g., the closure force is offloaded and/or diminished by the compression spring 404.

From the foregoing and with reference to the various figure drawings, those skilled in the art will appreciate that certain modifications can also be made to the present disclosure without departing from the scope of the same. For example, other resilient members, e.g., leaf springs, compressed gas, resilient bladder, spring washers and bellows, may be operably associated with any of the aforementioned configurations of utilized to generate a closure or sealing force at the jaw members. Moreover, the resilient members 204, 304 and 404 may work in combination with one or more springs located with the shaft 12 or housing 20 that are operatively associated with the drive assembly 130 to generate the necessary forces associated with tissue sealing.

Figure 5:
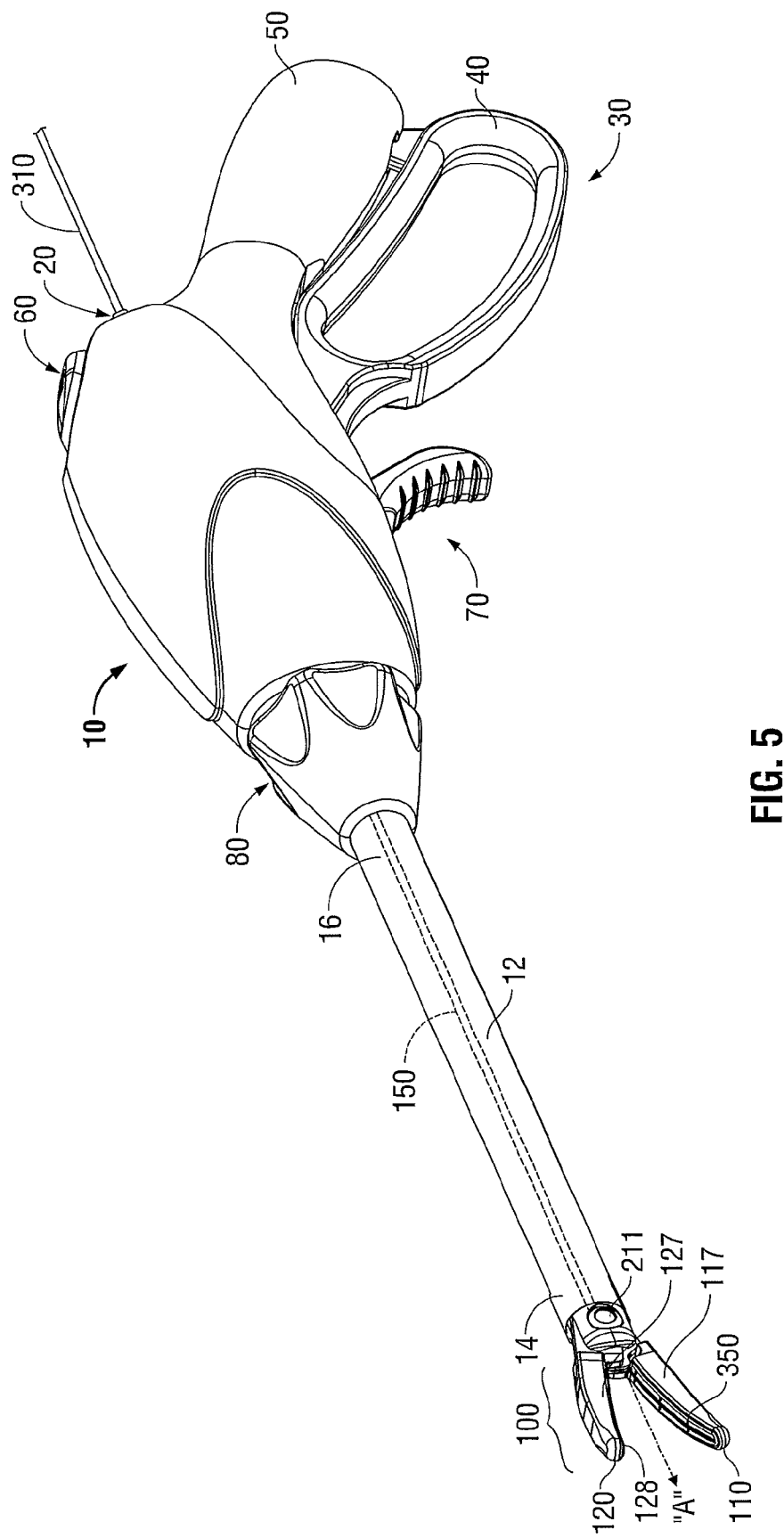
FIG. 5 is a side, perspective view of an endoscopic bipolar forceps showing an end effector assembly including jaw members in an open configuration according to still another embodiment of the present disclosure.

As best seen in FIG. 5, in order to achieve a desired spacing between the electrically conductive surfaces of the respective jaw members, e.g., jaw members 110 and 120, (i.e., gap distance) and apply a desired force to seal the tissue, one or both of the jaw members 110 and/or 120 may include one or more stop members 350 that limit the movement of the two opposing jaw members 110 and 120 relative to one another. The stop member 350 may be disposed on an inner facing surface of one or both of the jaw members 110 and 120. More particularly, stop member 350 extends from a seal surface 118a of seal plate 118 a predetermined distance according to the specific material properties (e.g., compressive strength, thermal expansion, etc.) to yield a consistent and accurate gap distance during sealing. In the illustrated embodiment, the stop members 350 extend from the seal surfaces 118a and 128a a distance that ranges from about 0.001 inches to about 0.006 inches. The gap distance between opposing sealing surfaces 118a and 128a during sealing may range from about 0.001 inches to about 0.006 inches and, preferably, between about 0.002 and about 0.003 inches. The configuration of a seal surface 118a with stop members 350 facilitates in maintaining a uniform distance between the jaw members 110 and 120 along the length thereof during tissue sealing.

For a more detailed description of the stop members 350 and operative components associated therewith, reference is made to commonly-owned United States Patent Publication No. 2009/0171350, filed Jan. 5, 2009.

Figure 6A:
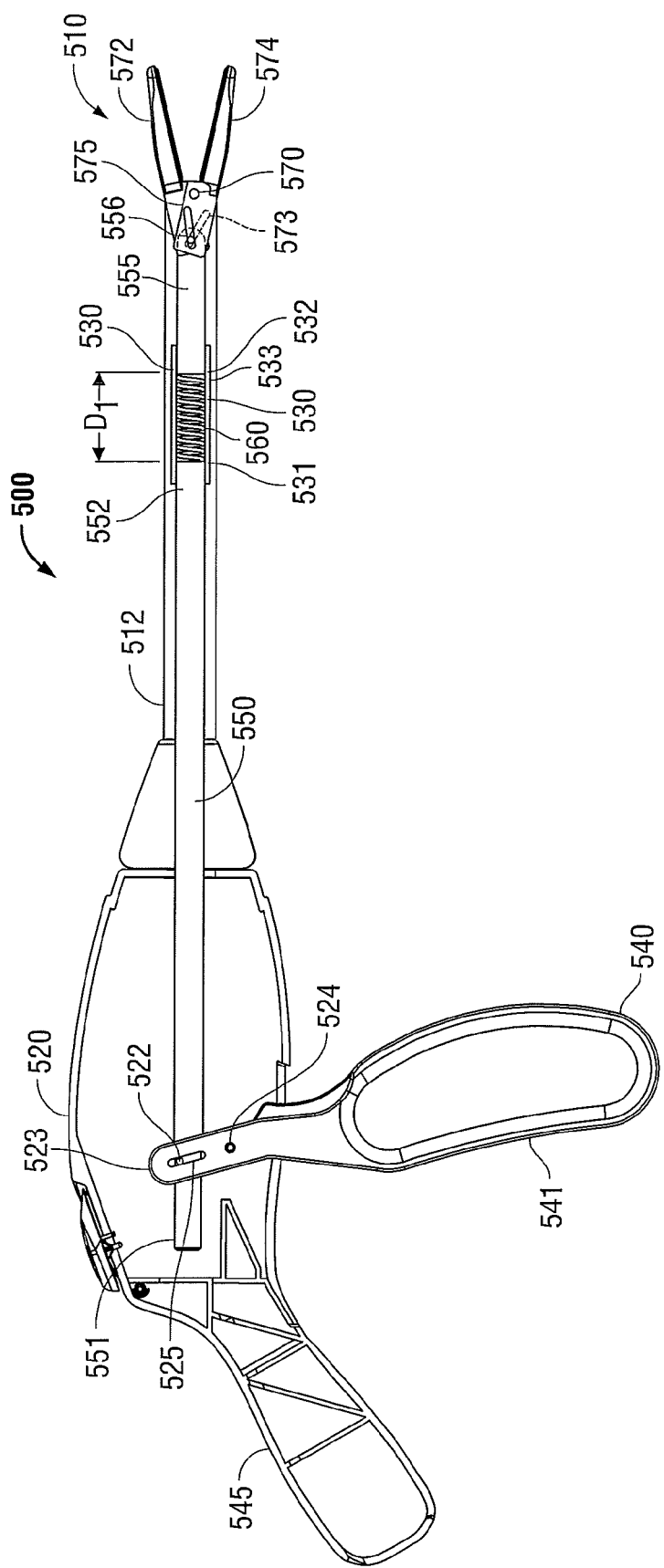
FIG. 6A is a side, cutaway view of an embodiment in accordance with the present disclosure having an end effector assembly with jaw members positioned in an open configuration.
Figure 6B:
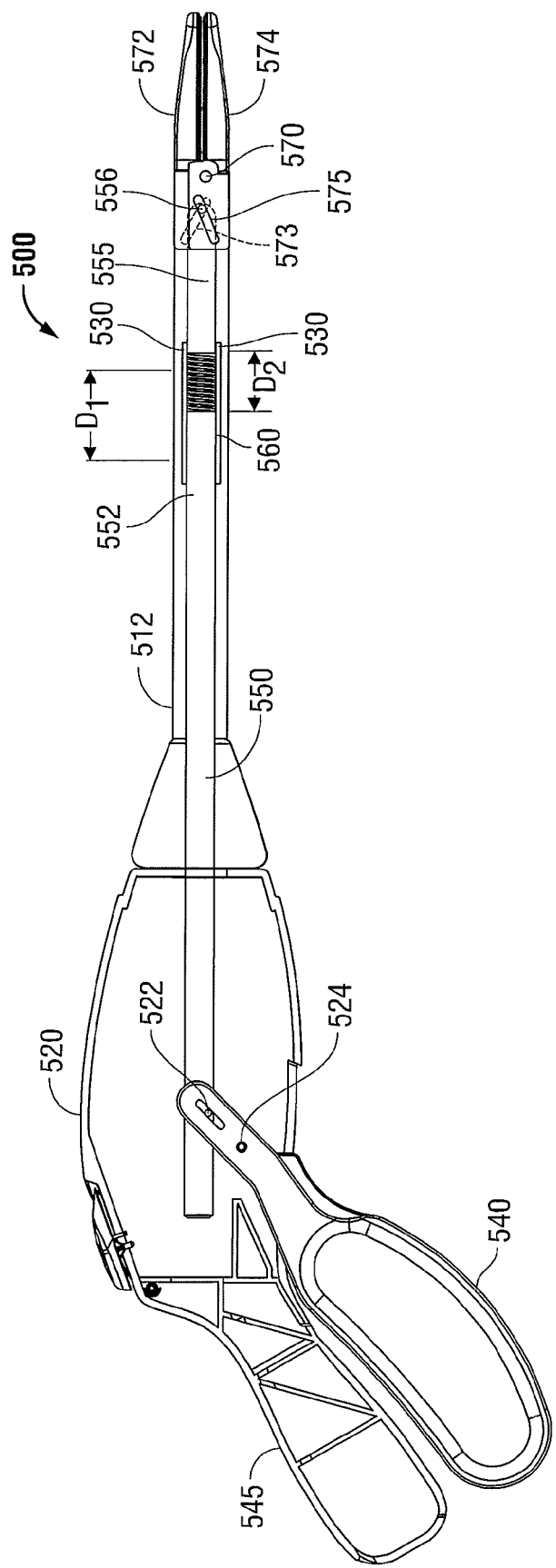
FIG. 6B is a side, cutaway view of the FIG. 6A embodiment having an end effector assembly with jaw members positioned in a closed configuration.

With reference to FIGS. 6A and 6B, an embodiment of a drive assembly 500 that is configured for use with forceps 10 is illustrated. End effector 510 is substantially identical to end effectors 100 and 300, and, in view thereof, and so as not to obscure the present disclosure with redundant information, only those features distinct to end effector 510 and drive assembly 500 will be described hereinafter.

The drive assembly includes a proximal drive rod 550 that is configured to translate longitudinally within shaft 512. A handle 540 having a gripping end 541 and an upper end 523 is pivotably mounted on a pivot 524 provided by a handle assembly 545. Upper end 523 of pivoting handle 540 includes a slot 525 defined therein and configured to receive a coupling pin 522 that, in turn, is operatively associated with a proximal end 551 of drive rod 550. By this arrangement, a proximal motion of a gripping end 541 of handle 540 (e.g., a squeezing motion) traverses slot 525 through an arc described by the upper end 523 of handle 540 as it rotates around pivot 524, and thus the cooperation between pin 522 and slot 525 translates drive rod 550 distally. At least a portion of a distal end 552 of drive rod 550 is slidably captured within a proximal portion 531 of guide 530, which confines the motion of drive rod 540 generally to a longitudinal axis of shaft 512.

A cam member 555 is slidably captured within a distal portion 532 of guide 530. A pin 556 associated with cam member 555 engages slots 573 and 575 defined within a proximal portion of jaw member 572 and 574, respectively, to facilitate the translation thereof between a mutually open configuration shown in FIG. 6A and a mutually closed configuration shown in FIG. 6B. As shown in FIGS. 6A and 6B, the orientation of slots 573 and 575 is arranged to cause jaw members 572, 574 to move from an open configuration FIG. 6A to a closed configuration of FIG. 6B as cam member 555 moves from a proximal position to a distal position. Alternatively, slots 573 and 575 may be arranged to cause jaw members 572, 574 to move in an opposite manner, e.g., from an open configuration to a closed configuration as cam member 555 moves from a distal position to a distal position.

Drive rod 550 is coupled to cam member 555 by a resilient member 560 that is captured within a center portion 533 of guide 530. Resilient member 560 may include a compression spring formed from a suitable metallic or non-metallic material, such as without limitation, spring steel, nylon, or fiberglass-epoxy composite. Resilient member 560 may additionally or alternatively be formed from an elastomeric material, such as without limitation, rubber, neoprene, and/or silicone.

During use, as handle 540 is squeezed, drive rod 550 is driven in a distal direction which, in turn, compresses resilient member 560, drives cam member 555 distally, and causes jaw members 572, 574 to move to a closed position. The force transferred from handle 540 and drive rod 550 to jaw members 572, 574 depends at least in part upon the spring rate of resilient member 560. For example, use of a resilient member 560 having a low spring rate (e.g., a relatively soft spring) would result in lower jaw clamping force, which may be suitable for smaller or more fragile tissue applications. Conversely, a higher spring rate (e.g., stiffer) would result in higher gripping forces being applied to tissue. Resilient member 560 may include a spring rate that is generally constant within its limits of elasticity, or, alternatively, may include a variable spring rate (e.g., a progressive spring rate that increases with compression or that decreases with compression). Resilient member 560 may include a step linear spring rate whereby two or more discrete, stepped spring rates are provided.

The disclosed drive arrangement may additionally include an adjustable resilient member 560, that may be adjusted in accordance with the requirements of a particular surgical procedure by changing a spring pre-loading via, e.g., a rotatable adjustment dial provided on the handle (not shown), a rotatable adjustment collar on the shaft 512 (not shown), and/or by providing one or more field-interchangeable resilient members that may be "loaded" into the instrument prior to use.

In yet another embodiment of a drive assembly 600 shown in FIGS. 7A and 7B, end effector 610 is substantially identical to end effectors 100 and 300, and, in view thereof, and so as not to obscure the present disclosure with redundant information, only those features distinct to end effector 610 and drive assembly 600 will be described hereinafter.

Figure 7A:
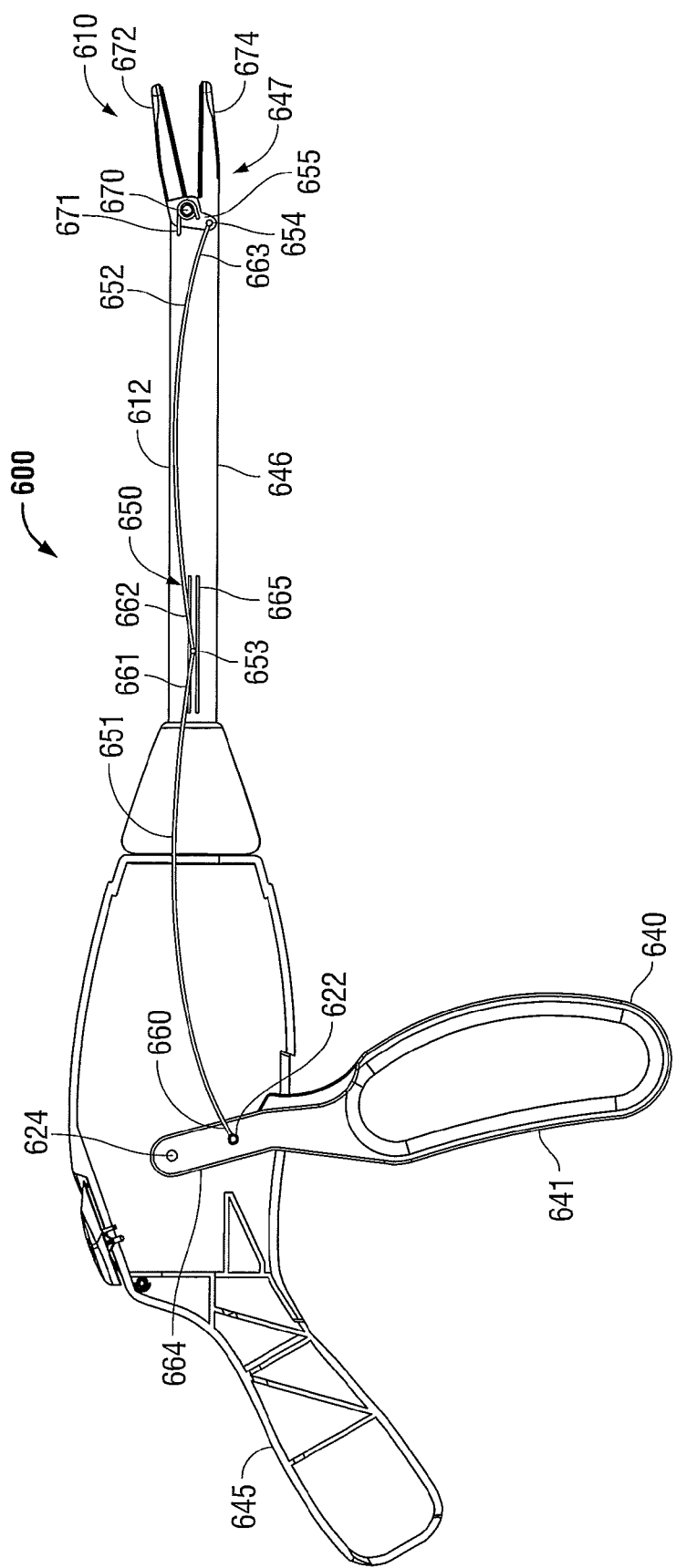
FIG. 7A is a side, cutaway view of an embodiment in accordance with the present disclosure having a hinged spring assembly and an end effector assembly with jaw members positioned in an open configuration.
Figure 7B:
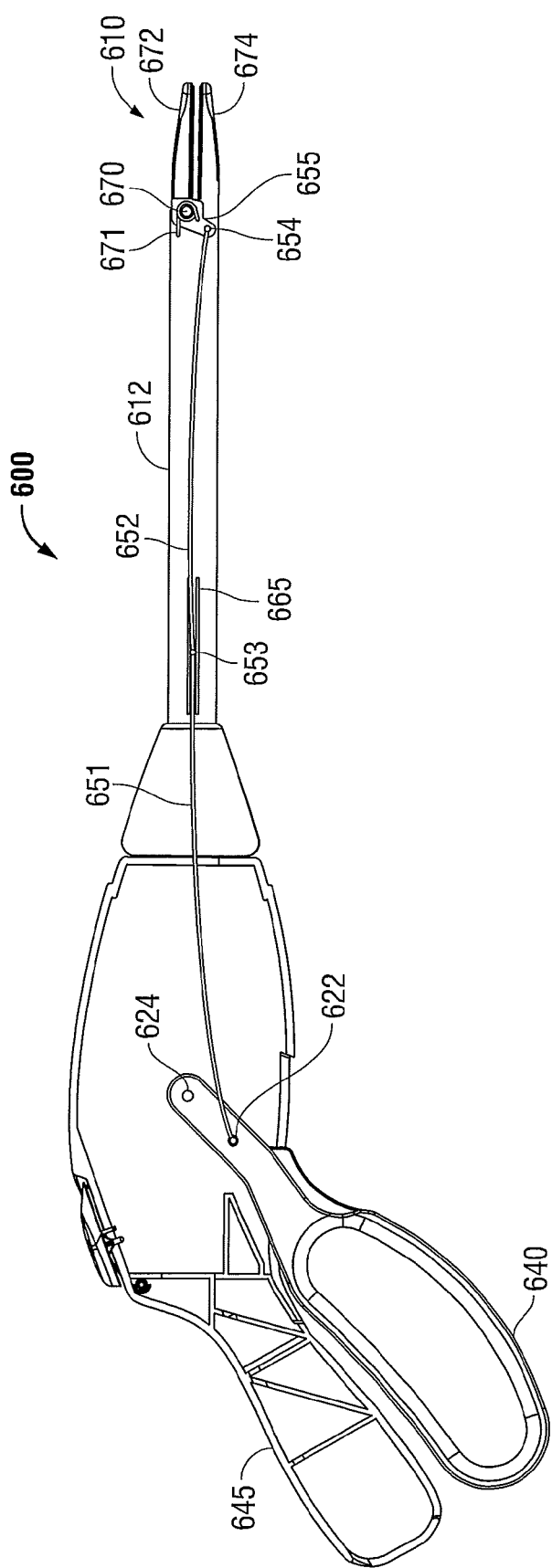
FIG. 7B is a side, cutaway view of the FIG. 7A embodiment having a hinged spring assembly and an end effector assembly with jaw members positioned in a closed configuration.

In the embodiment shown in FIGS. 7A and 7B, a lower stationary jaw 674 member is coupled to a distal end 647 of an elongated shaft 646. A movable upper jaw member 672 is rotationally translatable about a pivot point 670 to enable upper jaw member 672 to move relative to stationary jaw member 647 between an open position shown in FIG. 7A, and a closed position shown in FIG. 7B suitable for grasping tissue. A resilient member 671 biases upper jaw member 672 towards an open position. In the embodiment shown in FIGS. 7A and 7B, resilient member 671 includes a v-spring having one or more coils disposed about pivot point 670; however, any suitable resilient or spring-like member may be utilized, including without limitation, an elastomeric resilient member (e.g., rubber, silicone, neoprene), a leaf spring, and the like.

Upper jaw member 672 includes a proximal lever portion 655 that in the present embodiment is offset in a generally orthogonal manner to a longitudinal centerline of upper jaw member 672. A jaw spring mount 654 is included with proximal lever portion 655 of upper jaw member 672. A movable handle 640 is pivotably coupled to a housing 645 at a pivot point 624. Handle 640 includes a lever aim 664 that joins a grip portion 641 of the handle 640 to the pivot point 624. Lever arm 664 includes a handle spring mount 622.

A hinged leaf spring 650 operably connects at a proximal end 660 thereof to handle 640, and hinged leaf spring 650 operably connects at a distal end 663 thereof to proximal lever portion 655 of upper jaw member 672. More particularly, hinged leaf spring 650 includes at least a proximal spring section 651 and a distal spring section 652. Proximal spring section 651 and distal spring section 652 may be formed from any suitable resilient material, including without limitation, spring steel, fiber-reinforced composite (e.g., fiberglass, carbon fiber, and the like). Proximal spring section 651 and distal spring section 652 have a generally arcuate shape while in the relaxed state, and may have a flat, rectangular cross-sectional shape that may enhance rigidity and resist torsional forces. In some embodiments, proximal spring section 651 and distal spring section 652 may have a cross-sectional shape that is square, circular, ovoid, or polygonal. As shown in FIG. 8A, embodiments of a hinged spring 850 in accordance with the present disclosure include a first arcuate section 851 and a second arcuate section 852, each having a generally rectangular cross-section 853. A piano hinge 853 joins first arcuate section 851 and a second arcuate section 852. In some embodiments illustrated with reference to FIG. 8B, the hinged spring includes a first arcuate section 851' and a second arcuate section 852'. The arcuate sections 851' and 852' include a generally circular cross-section 853' and/or may be joined by a ball and socket-type hinge 853'.

A proximal end 660 of proximal spring section 651 is joined to a lever arm 664 of handle 640 at handle spring mount 622. A distal end of distal spring section 652 is joined to the proximal lever portion 655 of upper jaw member 672 at jaw spring mount 654. A proximal end 662 of distal spring section 652 is joined by hinge 653 to a distal end 661 of proximal spring section 651. Hinge 653 may include a piano-hinge arrangement, a ball-and-socket arrangement, and/or may include a living hinge. Hinged spring 650 may include two sections, as shown, or, alternatively, hinged spring 650 may include three or more sections joined by a hinge as described hereinabove.

During use, handle 640 may be drawn proximally, which, in turn, applies proximal tensile force to hinged spring 650 that causes the proximal spring section 651 and distal spring section 652 to extend from the relaxed, arcuate profile to a straighter profile. In this manner, a first portion of the proximal motion and/or force of handle 640 is absorbed by hinged spring 650 while the remainder of the proximal portion and/or force of handle 640 is applied to proximal lever portion 655 of upper jaw member 672, which, in turn, rotationally translates upper jaw 672 from an open position (e.g., as shown in FIG. 7A) to a closed position (e.g., FIG. 7B).

Advantageously, the force applied to upper jaw member 672, and thus to tissue grasped therebetween, may be controlled or limited by the selection of materials from which hinged spring 650 is formed and/or the dimensions of the spring sections, e.g., the elastomeric profile of the hinged spring assembly 650. For example, and without limitation, a hinged spring 650 having sections 651, 652 formed from material having a greater spring rate and/or having sections 651, 652 having a greater cross-section may increase the operational clamping force applied by jaw members 672, 674. Conversely, a hinged spring 650 having sections 651, 652 formed from material having a lower spring rate and/or having sections 651, 652 having a smaller cross-section may decrease the operational clamping force applied by jaw members 672, 674. In some embodiments, a first hinged spring section (e.g., a proximal section 651) may possess a first elastomeric profile and a second hinged spring section may possess a second elastomeric profile. By this arrangement, a variable, staged, or stepped application of jaw pressure may be achieved.

Figure 9:
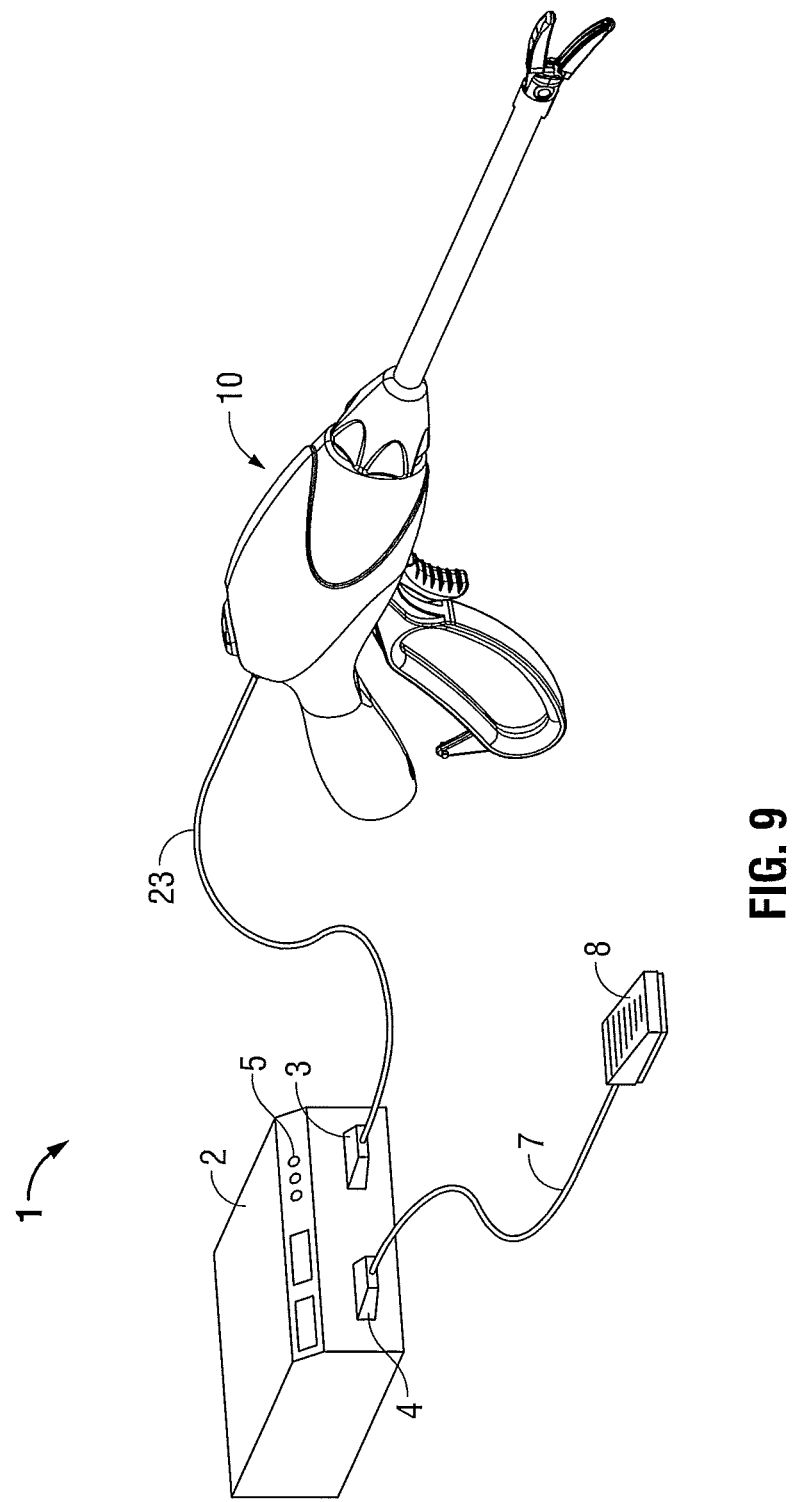
FIG. 9 is a schematic view of an electrosurgical system configured for use with an electrosurgical instrument according to an embodiment of the present disclosure.

Turning now to FIG. 9, an electrosurgical system 1 in accordance with the present disclosure is illustrated. The electrosurgical system 1 include a generator 2 that is operably coupled to bipolar forceps 10 by a cable 6. Cable 6 is detachably coupled to generator 2 via a connector 3. A footswitch 8 may be employed to provide an input to generator 2. Footswitch 8 is operably coupled to generator 2 via footswitch cable 4 and connector 4. Generator 2 includes a user interface 5 that may include, without limitation, input devices (e.g., switches, pushbuttons, continuously variable controls, touch screen, and the like) and/or displays (e.g., LCD displays, LED displays, alphanumeric displays, graphic displays, and the like). Generator 2 is configure to provide electrosurgical energy, e.g., radiofrequency or microwave energy, to forceps 10. In some embodiments, generator 2 includes the capability to provide an alternating electrosurgical signal in the range of about 200 KHz to about 3.3 MHz range. This electrosurgical signal can be a sinusoidal waveform operating in a continuous mode at a 100% duty cycle, or pulse modulated at a duty cycle of less than 100%. Depending on the surgical objective, the electrosurgical signal may have a 100% duty cycle for maximal cutting effect, may be pulse modulated at duty cycles ranging from 50% to 25% for less aggressive cutting or sealing, or, at a substantially lower duty cycle of approximately 6%, for coagulating or sealing. The electrosurgical signal may also be varied in intensity. The electrosurgical signal is applied to the patient via electrodes in either monopolar mode, or bipolar mode. In bipolar mode, both the active and return electrodes are at the surgical site, such as electrically conductive seal plates 118 and 128 so that the electrosurgical signal passes only through the tissue grasped between the jaw electrodes of the instrument.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

What is claimed is:

1. An endoscopic forceps, comprising:
   an elongated shaft having a proximal end and a distal end;
   an end effector assembly disposed at the distal end of the shaft and including a first jaw member and a second jaw member, at least one of the first and second jaw members movable relative to the other from a clamping position wherein the first and second jaw members cooperate to grasp tissue therebetween to an open position wherein the first and second jaw members are disposed in spaced relation relative to one another;
   a cam member configured to translate along a longitudinal axis defined through the shaft;
   a drive rod configured to translate along the longitudinal axis of the shaft; and
   a resilient member disposed proximate to at least one of the jaw members and configured to operably couple a distal end of the of the drive rod to a proximal end of the cam member, wherein at least one of the first and second jaw members includes at least one cam slot defined therein configured to receive the cam member such that longitudinal movement of the resilient member along the longitudinal axis of the shaft moves the first and second jaw members from the clamping position to the open position.

2. An endoscopic forceps according to claim 1, wherein the resilient member is selected from the group consisting of a compression spring and a leaf spring.

3. An endoscopic forceps according to claim 1, further comprising a housing having a handle that extends therefrom that is configured to translate the drive rod distally.

4. An endoscopic forceps according to claim 1, wherein the resilient member provides a closure force of about 3 kg/cm2 to about 16 kg/cm2.

5. An endoscopic forceps according to claim 1, further including a plurality of non-conductive stop members disposed on an inner facing surface of at least one of the first and second jaw members, the non-conductive stop members configured to maintain a uniform distance between the first and second jaw members along a length thereof when disposed in the clamping position.

6. An endoscopic forceps according to claim 5, wherein the plurality of non-conductive stop members extend from the inner facing surface a distance that ranges from about 0.001 inches to about 0.006 inches.

7. An endoscopic forceps according to claim 1, further including a guide disposed around at least a portion of the drive rod, the resilient member, or the cam member.

8. An endoscopic forceps, comprising:
   a housing having a shaft that extends therefrom defining a longitudinal axis therethrough;
   an end effector assembly operatively connected to a distal end of the shaft and including a first jaw member and a second jaw member, the first jaw member movable relative to the second jaw member from an open position wherein the first and second jaw members are disposed in spaced relation relative to one another to a closed position wherein the first and second jaw members cooperate to grasp tissue therebetween;
   a resilient member operably coupled to the first jaw member and configured to bias the first jaw member toward the open position;
   a hinged spring operably coupled at a distal end thereof to the first jaw member, the hinged spring including a proximal portion and a distal portion separated by a hinge, the hinge operably coupled to at least a portion of the shaft; and
   a handle extending from the housing, operably coupled to a proximal end of the hinged spring and configured to translate a proximal end of the hinged spring along the longitudinal axis of the housing.

9. An endoscopic forceps according to claim 8, wherein at least a portion of the hinged spring includes an arcuate contour along a longitudinal axis thereof.

10. An endoscopic forceps according to claim 8, wherein one end of the resilient member is operably coupled to a distal end of the shaft.

11. An endoscopic forceps according to claim 8, wherein the hinged spring provides a closure force of about 3 kg/cm2 to about 16 kg/cm2.

12. An endoscopic forceps according to claim 8, further including a plurality of non-conductive stop members disposed on an inner facing surface of at least one of the first and second jaw members, the non-conductive stop members configured to maintain a uniform distance between the first and second jaw members along a length thereof when disposed in the closed position.

13. An endoscopic forceps according to claim 12, wherein the plurality of non-conductive stop members extend from the inner facing surface a distance that ranges from about 0.001 inches to about 0.006 inches.

14. An endoscopic forceps according to claim 8, wherein at least a portion of the hinged spring has a cross-sectional shape selected from the group consisting of square, rectangular, circular, and ovoid.

15. An electrosurgical system, comprising:
an electrosurgical generator; and
an endoscopic forceps configured to operably couple with the electrosurgical generator, the endoscopic forceps comprising:
an elongated shaft having a proximal end and a distal end;
an end effector assembly disposed at the distal end of the shaft and including a first jaw member and a second jaw member, at least one of the first and second jaw members movable relative to the other from a clamping position wherein the first and second jaw members cooperate to grasp tissue therebetween to an open position wherein the first and second jaw members are disposed in spaced relation relative to one another;
a cam member configured to translate along a longitudinal axis defined through the shaft;
a drive rod configured to translate along the longitudinal axis of the shaft; and
a resilient member disposed proximate to at least one of the jaw members and configured to operably couple a distal end of the of the drive rod to a proximal end of the cam member, wherein at least one of the first and second jaw members includes at least one cam slot defined therein configured to receive the cam member such that longitudinal movement of the resilient member along the longitudinal axis of the shaft moves the first and second jaw members from the clamping position to the open position.

16. An electrosurgical system according to claim 15, wherein the resilient member of the endoscopic forceps is selected from the group consisting of a compression spring and a leaf spring.

17. An electrosurgical system according to claim 15, wherein the endoscopic forceps further comprises a housing having a handle that extends therefrom that is configured to translate the drive rod distally.

18. An electrosurgical system according to claim 15, wherein the resilient member of the endoscopic forceps provides a closure force of about 3 kg/cm2 to about 16 kg/cm2.

19. An electrosurgical system according to claim 15, wherein the endoscopic forceps further comprises a plurality of non-conductive stop members disposed on an inner facing surface of at least one of the first and second jaw members, the non-conductive stop members configured to maintain a uniform distance between the first and second jaw members along a length thereof when disposed in the clamping position.

* * * * *